United States Patent [19]

Ruiz

[11] Patent Number: 5,895,404
[45] Date of Patent: Apr. 20, 1999

[54] APPARATUS AND METHODS FOR PERCUTANEOUSLY FORMING A PASSAGEWAY BETWEEN ADJACENT VESSELS OR PORTIONS OF A VESSEL

[76] Inventor: Carlos E. Ruiz, 1747 N. Country La., Pasadent, Calif. 91107

[21] Appl. No.: 08/939,180

[22] Filed: Sep. 29, 1997

[51] Int. Cl.⁶ .................................................. A61B 17/34
[52] U.S. Cl. ...................... 606/185; 607/122; 607/126; 607/125; 604/53; 604/280; 604/264; 600/524; 600/11; 600/12; 606/186; 606/151; 606/167
[58] Field of Search ........................... 606/185, 186, 606/151, 167; 607/122, 125, 126; 604/53, 280, 264; 600/524, 11, 12

[56] References Cited

U.S. PATENT DOCUMENTS

| | | | |
|---|---|---|---|
| 3,874,388 | 4/1975 | King et al. | 606/213 |
| 5,108,420 | 4/1992 | Marks | 606/213 |
| 5,334,217 | 8/1994 | Das | 606/213 |
| 5,624,430 | 4/1997 | Eton et al. | 606/1 |

FOREIGN PATENT DOCUMENTS

WO 97/13463  4/1997  WIPO .

OTHER PUBLICATIONS

Castaneda, Aldo R. MD, PhD, "From Glenn to Fontan: A Continuing Evolution," *Supplement to Circulation*, vol. 86, No. 5 (supplement), (Nov. 1992), pp. II80–II84.

Cowgill, L. Douglas MD, "The Fontan Procedure: A Historical Review," *The Annals of Thoracic Surgery*, vol. 51, No. 6, (Jun. 1991) pp. 1026–1030.

Laks, Hillel MD et al., "Modification of the Fontan Procedure: Superior Vena Cava to Left Pulmonary Artery Connection and Inferior Vena Cava to Right Pulmonary Artery Connection with Adjustable Atrial Septal Defect," *Circulation*, vol. 91, No. 12, (Jun. 1995), pp. 2943–2947.

Laschinger, John C. MD et al., "Intermediate Results of the Extracardia Fontan Procedure," *The Annals of Thoracic Surgery*, vol. 62, No. 5, (Nov. 1996), pp. 1261–1267.

Mainwaring, Richard D. MD et al., "Bidrectional Glenn: Is Accessory Pulmonary Blood Flow Good or Bad?," *Supplement to Circulation*, vol. 92, No. 9, (Nov. 1995), pp. II294–II297.

Narayan, Ravi et al., "Bidirectional Glenn Shung: A Step in the Right Direction," *Indian Heart Journal*, vol. 48, No. 4, (Jul.–Aug. 1996), pp. 375–380.

*Primary Examiner*—Michael Buiz
*Assistant Examiner*—Tan-Uyen T. Ho
*Attorney, Agent, or Firm*—Fish & Neave; Nicola A. Pisano

[57] ABSTRACT

Apparatus and methods for percutaneously forming a passageway between adjacent vessels, a vessel and an organ, or different regions of an organ are provided comprising first and second catheters carrying distally positioned electromagnets. The first and second catheters are percutaneously advanced to positions within a body so that the distal endfaces oppose one another and magnetically attract one another, causing the lumens of the catheters to become aligned. A cutting wire is then advanced out of the first lumen, through the thickness of the tissue captured between the catheters, and into the second lumen. The cutting wire may be advanced fully through the second catheter so that it exits the patient, and upon removal of the first and second catheters, serves as a guide wire. Methods of percutaneously performing surgery are also provided.

20 Claims, 5 Drawing Sheets

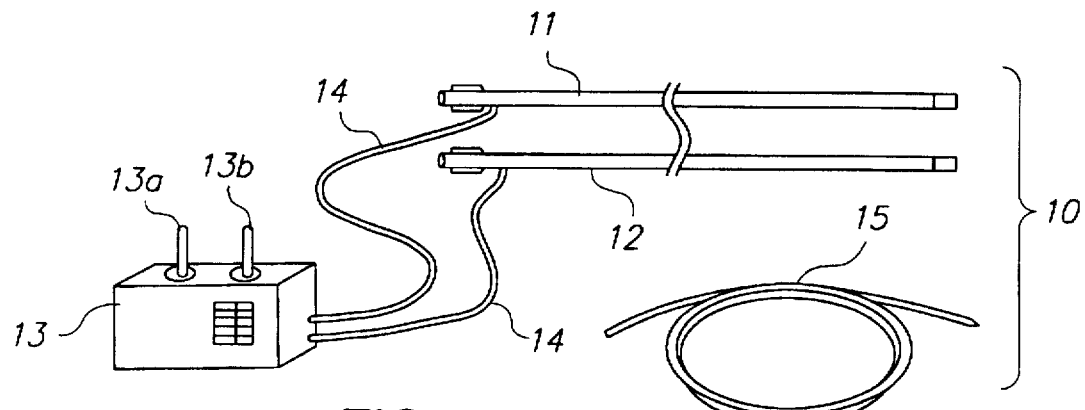
FIG. 1
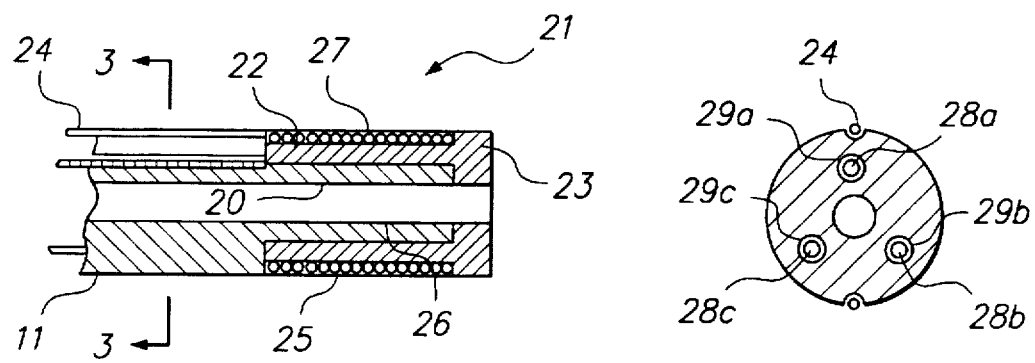 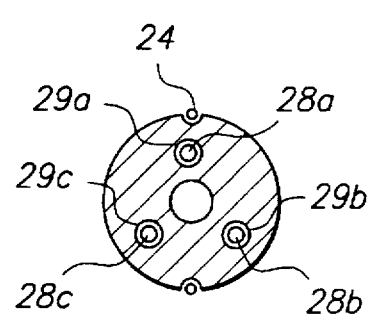
FIG. 2  FIG. 3
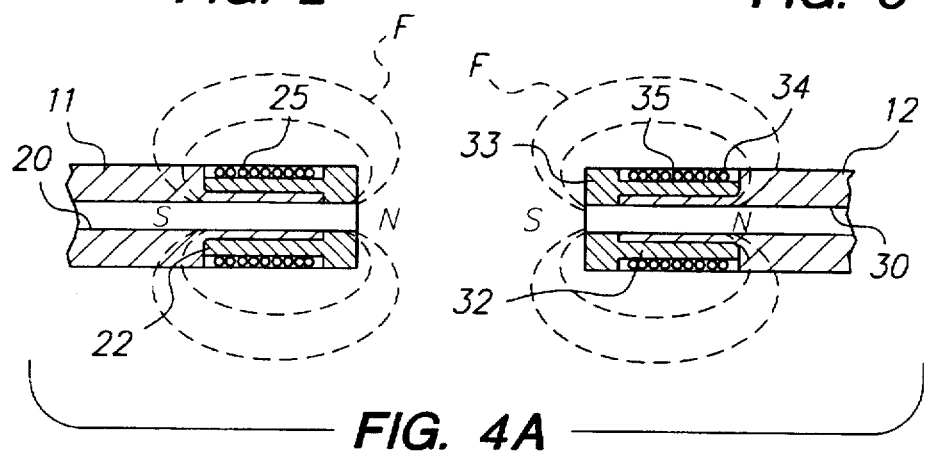
FIG. 4A
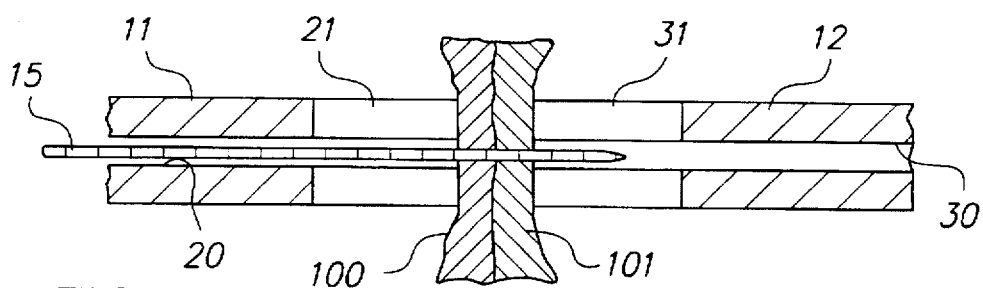
FIG. 4B

APPARATUS AND METHODS FOR PERCUTANEOUSLY FORMING A PASSAGEWAY BETWEEN ADJACENT VESSELS OR PORTIONS OF A VESSEL

FIELD OF THE INVENTION

The present invention relates to apparatus and methods for percutaneously forming connections between adjacent vessels, an organ and vessel, or different regions of an organ, to enable fluid communication therebetween. More particularly, the present invention provides a catheter system that enables the formation of a passageway across tissue disposed between two vessels, a vessel and an organ, or portions of an organ, wherein the passageway has a predetermined trajectory.

BACKGROUND OF THE INVENTION

A number of congenital defects are encountered in pediatric cardiac surgery wherein it is desirable to create a passageway between adjacent vessels or adjacent regions of an organ. For example, congenital lesions frequently involve an obstruction of blood flow to the lungs, such as pulmonary atresia with, or without intact ventricular septum, Tetralogy of Fallot, complex single ventricle anatomy, and pulmonary valve stenosis.

A first step in treating such defects typically involves placing a graft between the systemic arterial system and the pulmonary arteries to supply blood to the lungs. Such a graft is often referred to as "Blalock-Taussig shunt" or "B-T" shunt, and is placed between the native subclavian artery and the pulmonary artery. To install a typical Blalock-Taussig shunt, the surgeon exposes the mediastinum (the contents of the middle of the chest between the two lungs), the pulmonary artery and the subclavian artery. A graft of suitable synthetic material (e.g., PTFE) is then anastomosed between the arteries, so that flow passes from the subclavian artery to the lungs via the pulmonary artery.

In the Glenn procedure, often performed as the second stage of treating pulmonary atresia and single ventricle anatomy, the distal end of the superior vena cava is anastomosed to the superior wall of the right pulmonary artery, while the proximal end of the superior vena cava is either occluded or anastomosed to the inferior wall of the right pulmonary artery. It would therefore be desirable to provide apparatus to percutaneously anastomose the pulmonary artery to the superior vena cava.

In the Fontan procedure, which is often used to treat complex single ventricle anatomy, the proximal end of the superior vena cava is anastomosed to the inferior wall of the right pulmonary artery, and the right atrium closed off, so that there is little or no communication between either the inferior vena cava or the superior vena cava and the right atrium. Isolation of the vena cava from the right atrium also minimizes the impact of an atrial septal defect. Conventional treatment of single ventricle anatomy is generally performed in two surgical stages, to enable the heart to gradually accommodate the hemodynamic impact of the procedure. However, repeated surgeries cause significant trauma to the patient, require long recuperation times, and pose serious risks of mortality. It therefore would be desirable to enable at least one stage of a complicated procedure, such as the Glenn or Fontan procedure, to be accomplished using an interventional (i.e., percutaneous), rather than surgical, approach.

In other medical applications, such as treatment of coronary artery disease and in some cases of pulmonary vascular atresia, it is often desirable to form a passageway through an occlusion. Unfortunately, balloon dilatation catheters generally can only be used where there is not total occlusion, while cutting catheters, such as atherectomy catheters, pose a risk of dissecting the vessel. It would therefore be desirable to provide apparatus and methods that would enable an opening to be formed through an occluded pulmonary valve or occluded vessel with a high degree of certainty of the trajectory of the puncture.

In view of the foregoing, it would therefore be desirable to provide apparatus that enables the formation of a passageway between adjacent vessels, adjacent regions of an organ, or between an organ and an adjacent vessel, to establish a flow path therebetween.

SUMMARY OF THE INVENTION

In view of the foregoing, it is an object of this invention to provide apparatus and methods for percutaneously forming a passageway between adjacent vessels, an organ and an adjacent vessel, or adjacent regions of an organ, wherein the trajectory of the device forming the passageway is predetermined.

It is another object of this invention to provide apparatus and methods for interventionally performing-at least one stage of a multi-stage pediatric cardiac surgical procedure, such as the completion of a bidirectional Glenn or Fontan procedure.

It is another object of the present invention to provide apparatus and methods for percutaneously forming a passage through an obstructive lesion contained within an organ or vessel, such as opening a congenitally unperforated pulmonary valve, with reduced risk of perforation of the septum.

These and other objects of the present invention are accomplished by providing apparatus and methods for percutaneously forming a passageway between adjacent vessels, a vessel and an organ, or through an obstruction located between different regions of an organ or vessel. The apparatus comprises a first catheter carrying a magnetic end region and a cutting device, and a second catheter carrying a magnetic end region and a lumen into which the cutting device may be extended.

A first embodiment of the apparatus of the present invention comprises a pair of flexible catheters, each having a lumen and an electromagnet disposed on its distal end. The electromagnets are coupled to a suitable power source, and have their windings (or power terminals) arranged to induce opposite poles on the distal end faces of the respective catheters. The catheters are percutaneously advanced to positions within a body so that the distal endfaces oppose one another and magnetically attract one another.

When the endfaces are magnetically coupled to one another, the lumens of the first and second catheters are aligned. A cutting wire is then advanced out of the first lumen, through the thickness of the tissue (or obstruction) captured between the endfaces of the catheters, and into the second lumen. The cutting wire may then be advanced fully through the second catheter so that it exits the patient. The electromagnets may be de-energized and the first and second catheters withdrawn, leaving the cutting wire in position as a guide wire.

In an alternative embodiment, the cutting wire includes means for engaging the second lumen after the cutting wire passes through the tissue. After the cutting wire passes into and is engaged in the second lumen, the electromagnets are de-energized and the catheters are withdrawn. As the second catheter is withdrawn, it pulls the cutting wire through the passage traversed by the second catheter, until the distal end of the cutting wire exits the patient's body.

In either of the foregoing examples, after the electromagnet-bearing catheters are removed, a series of catheters of increasing diameter may be passed along the cutting wire to enlarge the diameter of the opening in the intervening tissue. In addition, the cutting wire may be used as a guide wire for deploying a prosthesis, such as a stent or graft, to seal against leakage into the intervening tissue.

Illustrative methods of using the apparatus of the present invention to percutaneously perform surgery, such as pediatric cardiac surgery to correct congenital defects, are provided.

BRIEF DESCRIPTION OF THE DRAWINGS

Further features of the invention, its nature and various advantages will be more apparent from the accompanying drawings and the following detailed description of the preferred embodiments, in which:

FIG. 1 is a side view of an illustrative embodiment of apparatus constructed in accordance with the present invention;

FIG. 2 is a cross-sectional view of the distal end of a catheter constructed in accordance with the present invention;

FIG. 3 is a sectional view of the distal end of the apparatus of FIG. 2 along the view line 3—3;

FIGS. 4A and 4B are cross-sectional views depicting use of the apparatus to form an opening between adjacent vessels;

DETAILED DESCRIPTION OF THE INVENTION

Figure 5A:
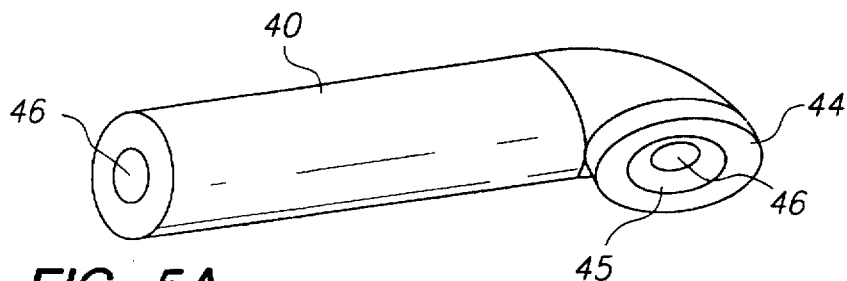
FIGS. 5A and 5B are, respectively, a perspective view and a side view of the distal ends of an alternative embodiment of the apparatus of FIG. 1.

The present invention relates generally to apparatus and methods for forming extracorporeal passageways between adjacent vessels, an organ and a vessel, or through obstructions located within a vessel or between regions of an organ. More particularly, the present invention permits creation of a passageway through tissue captured between the distal ends of a pair of catheters, wherein the trajectory of the passageway is predetermined by the relative orientation of the catheters. In addition, the apparatus of the present invention serves as (or facilitates the placement of) a guide wire that enables the passageway to be readily enlarged, and facilitates the deployment of prostheses.

Referring to FIGS. 1 and 2, illustrative apparatus 10 constructed in accordance with the present invention is described. Apparatus 10 includes catheters 11 and 12 coupled to power source 13 by cables 14, and flexible cutting wire 15. Catheter 11 comprises a flexible material commonly used in catheter construction, such as polyvinyl chloride or polyethylene, and includes lumen 20 and electromagnet 21 disposed on its distal end.

Electromagnet 21 illustratively comprises thin ferromagnetic annular element 22 including flange 23 that forms the distal endface of catheter 11, and insulated wire 24 wrapped in coil 25 around the circumference of annular element 22. Annulus 22 preferably is disposed within stepped region 26 of catheter 11, so that the loops of coil 25 formed by insulated wire 24 do not project beyond the outer diameter of catheter 11. The ends of insulated wire 24 extend to the proximal end of catheter 11 in grooves, where they terminate in terminals that connect to one of the cables 14. A suitable potting material or adhesive 27 may be employed to retain the loops of coil 25 in position, and may in addition be covered with a suitable biocompatible sheathing (not shown) that provides a leak-tight seal for the electromagnet.

Catheter 11 may in addition include means for deflecting the endface of the catheter away from the longitudinal axis, such as described in U.S. Pat. No. 4,543,090 to McCoy or any of U.S. Pat. Nos. 5,527,279, 5,497,784, 5,389,073 or 5,330,466 to Imran. The tip-deflecting elements of all of the aforementioned patents are incorporated herein by reference. Those patents generally teach that the tip of a catheter may be made steerable by using nickel-titanium elements (e.g., wires) arranged in lumens extending through the catheter, and that by selectively heating (or pulling), the wires, the tip of the catheter can be made to deflect away from the longitudinal axis of the catheter. FIG. 3 illustrates an arrangement of wires 28a–28c disposed in catheter 11 in lumens 29a–29c, respectively, in the same manner as described with respect to FIG. 3 of U.S. Pat. No. 5,497,784. It is to be understood that power source 13 of the present invention may incorporate the appropriate electronic components described in U.S. Pat. No. 5,497,784 to operate wires 28a–28c, via operation of joystick 13a, to cause the distal endface to deflect off-axis a desired distance. Of course, other mechanisms for deflecting the tip of catheter 11 also may be employed.

Catheter 12 of the FIGS. 1 and 2 is constructed in the same fashion as described hereinabove for catheter 11, and includes lumen 30 and electromagnet 31 comprising annular element 32 having flange 33, and insulated wire 34 forming coil 35, arranged as described for catheter 11. Cables 14 are connected to catheters 11 and 12 so that the current flows through coils 25 and 35 of catheters 11 and 12. Magnetic flux lines F generated by the current passing through coils 25 and 35 create magnetic poles N and S of opposite polarity on the distal endfaces of the respective catheters. Thus, for example, the distal endface of catheter 11 forms a north magnetic pole N while the distal endface of catheter 12 forms a south magnetic pole S. Accordingly, when the distal regions of catheters 11 and 12 are energized and brought into proximity with one another, the magnetic fields generated by electromagnets 21 and 31 are sufficient to cause the distal endfaces of the catheters to attract one another, even through a region of intervening tissue.

Power source 13 includes circuitry for converting common line voltage (e.g. 120 V) to a value appropriate for use in energizing electromagnets 21 and 31. For example, since for safety reasons it is generally not desirable to employ low frequency or direct current in medical devices, power source 13 may include conventional circuitry for generating a high frequency (e.g., greater than 200 kHz) voltage signal. Power source 13 also may include joysticks 13a and 13b, as described in the above-incorporated patents, for individually steering the distal ends of catheters 11 and 12.

In one preferred embodiment of the apparatus of the present invention, lumens 20 and 30 extend to the proximal ends of catheters 11 and 12. As illustrated in FIGS. 4A and 4B, catheter 11 may be percutaneously advanced in a vessel to a location wherein distal endface abuts wall 100 of a vessel or organ. Catheter 12 is then routed via an alternate pathway so that the distal endface abuts against wall 101 of a vessel or organ in juxtaposition to catheter 11. The orientations of the distal ends of catheters 11 and 12 may be confirmed using conventional imaging techniques (e.g., fluoroscopy). Power source 13 is then activated to energize electromagnets 21 and 31, causing the electromagnets to attract one another across a thickness of intervening tissue 100, 101.

Flexible cutting wire 15, which preferably comprises a high strength non-magnetic metal, metal alloy, or plastic, is then advanced through lumen 20 from the proximal end of the lumen to the distal end of catheter 11. Cutting wire 15 preferably includes a sharpened tip, so that it may be pushed to pierce the tissue disposed between catheters 11 and 12, and into lumen 30 of catheter 120. Because the electromagnets will tend to be self-centering with respect to one another, lumens 20 and 30 will be aligned across the intervening tissue 100, 101, and provide a predetermined trajectory for the cutting wire as it passes through the tissue.

Cutting wire 15 may then be advanced through lumen 20, across tissue 100, 101 and through lumen 30 to its proximal end. Once cutting wire 30 exits the proximal end of catheter 12, catheters 11 and 12 may be withdrawn, while leaving cutting wire 15 in place. Cutting wire 15 may then serve as a guide wire in subsequent steps of the procedure, or may be joined to a conventional guide wire and used to pull that guide wire through the passageway formed in the tissue.

Figure 5B:
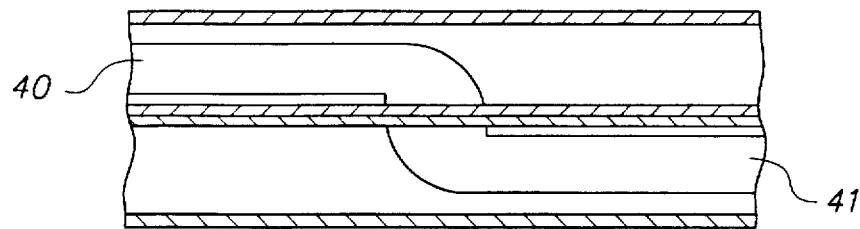

Referring now to FIGS. 5A and 5B, an alternative embodiment of the apparatus of FIG. 1 is described. Catheters 40 and 41 are similar in construction to catheters 11 and 12 described hereinabove, except that the distal endfaces of catheters 41 and 42 are modified so that the lumens exit from the side, rather than the end, of the catheters. Endface 44 shown in FIG. 5A also may include conical region 45 that assists in guiding the cutting wire into lumen 46. In this embodiment, the ferromagnetic annular elements are shorter, and the insulated coils formed by the insulated wires are arranged parallel to, rather than transverse to, the longitudinal access of the catheters. The catheters are positioned so that the side-looking endfaces overlap, as shown in FIG. 5B, and the cutting wire is then advanced, as described hereinabove.

Advantageously, catheters 40 and 41 may omit a mechanism for deflecting the tips of the catheters, and therefore may have reduced diameters compared to the catheters illustrated in FIG. 1. Accordingly, the catheters of FIGS. 5A and 5B may be used in smaller diameter vessels, for example, in creating interconnections between adjacent arteries and veins, or between an artery and a vein. In addition, combinations of the catheters of FIGS. 1 and 5 may be employed, for example, to form a channel between a small diameter vessel and a chamber of an organ (e.g., the left ventricle). See, e.g., U.S. Pat. No. 5,665,548 to Nelson et al. and U.S. Pat. No. 5,409,019 to Wilk.

Figure 6A:
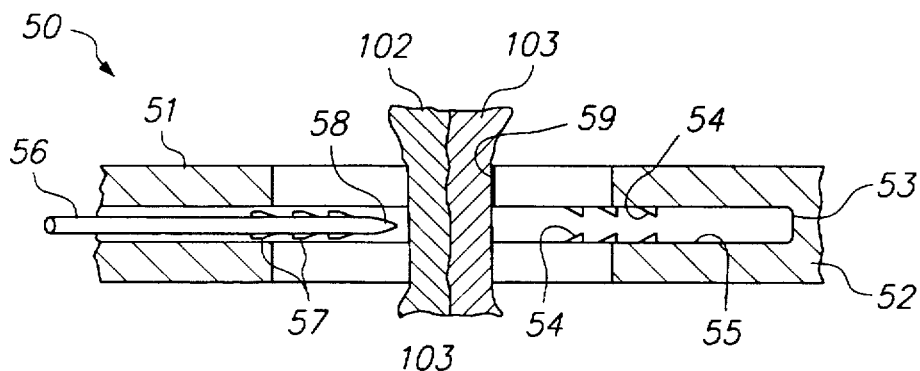
FIGS. 6A and 6B are cross-sectional views of another alternative embodiment of the apparatus of FIG. 1.
Figure 6B:
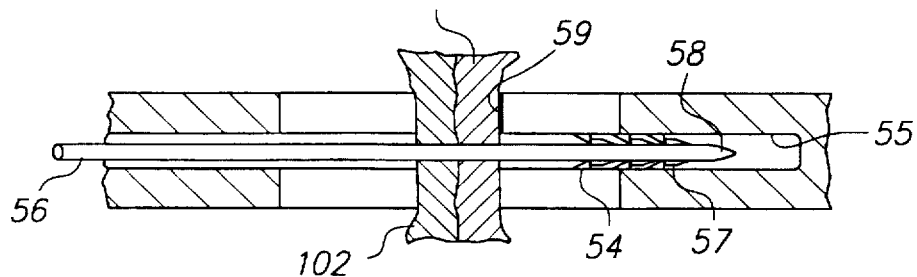

Referring now to FIGS. 6A and 6B, yet another alternative embodiment of the apparatus of the present invention is described. Apparatus 50 includes catheters 51 and 52, where catheter 51 is identical to catheter 11 described above with respect to FIG. 4A (the detail of the electromagnets are omitted for clarity). Catheter 52 is similar to catheter 12 of FIG. 4A, but differs in that lumen 53 does not extend to the proximal end of catheter 52. Instead, lumen 53 forms a "blind" bore, and includes a plurality of ribs 54 extending from inner surface 55 of the bore. As illustrated in FIG. 6A, in this embodiment cutting wire 56 includes one of more angled barbs 57 disposed on its circumference near the distal end.

As shown in FIG. 6B, when cutting wire 56 is advanced through tissue 102, 103 disposed between the endfaces of catheters 51 and 52, tip 58 of cutting wire 56 is guided into lumen 53. When cutting wire 56 is fully extended into lumen 53, ribs 54 engage barbs 57, thereby preventing withdrawal of cutting wire 56 from catheter 52. Catheter 52 may then be withdrawn from the patient, pulling cutting wire 56 through lumen 20, through the passageway in the tissue, and out of the patient's body through the entry path used by catheter 52. Cutting wire may then be employed as a guide wire, or have a guide wire substituted in its place as described hereinabove.

Alternatively, once cutting wire 56 is captured in catheter 52, catheter 51 may be withdrawn over cutting wire 56, while catheter 52 is left in position. Endface 59 of catheter 52 may then be used as an "anvil" for treatment devices subsequently deployed on cutting wire 56. For example, if the opening through the tissue is to be enlarged, a catheter having a sharpened annular edge may be advanced along cutting wire 56. Upon reaching tissue 102, 103, the catheter may be advanced so that it cuts a core of tissue against endface 59 of catheter 52.

As another example, endface 59 of catheter 52 may be used as a "stop" for positioning a stent or graft delivery device deployed along cutting wire 56. In this instance, the clinician can sense that the stent or graft is properly positioned for delivery in the passageway formed between the vessels by advancing the stent or graft delivery device along cutting wire 56 until the distal end of the delivery device abuts against endface 59 of catheter 52. Other applications for the embodiment of FIG. 6 will be apparent to those of skill in the art of interventional procedures.

It is to be understood that the embodiments of apparatus described hereinabove are merely illustrative. For example, lumens 20 and 30 need not be centrally located, but may be disposed anywhere in the cross-section of the catheter, so long as the electromagnets are configured to align the lumens when disposed in opposing relation across a thickness of tissue. The ferromagnetic annular elements of FIG. 1 also may comprise several sections having their coils wound so as to create alternating polarities.

Figure 7:
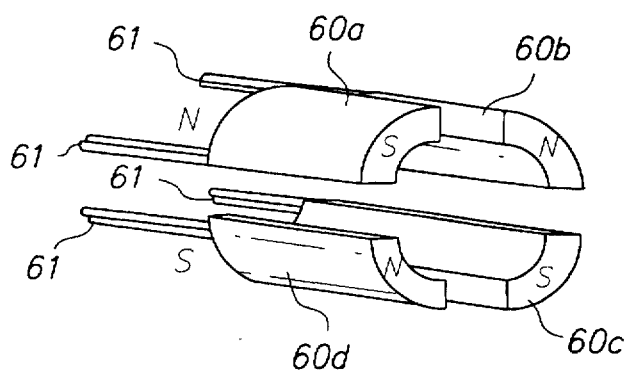
FIG. 7 is an exploded view of a multi-sector electromagnet constructed in accordance with the present invention wherein the catheter is omitted for clarity.

For example, in FIG. 7, the annular element of FIG. 1 is divided into four quadrants 60a-60d, each having its own electric coil formed by insulated wires 61. Adjacent coils are wound in opposite directions (or are connected to opposite polarities at power source 13) to create different magnetic poles at the endfaces of the quadrants (indicated by letters N and S in FIG. 7). The opposing catheter also includes an endface divided into four quadrants of alternate polarity. Applicant expects that the use of multiple poles on the endfaces of the opposing catheters will further enhance the self-alignment of the lumens of the respective catheters.

In addition, as will be apparent to one of skill in the art of interventional devices, cutting wires 15 and 56 of the present invention may include active elements, for example, radiofrequency, laser or mechanical cutting elements.

Figure 8A:
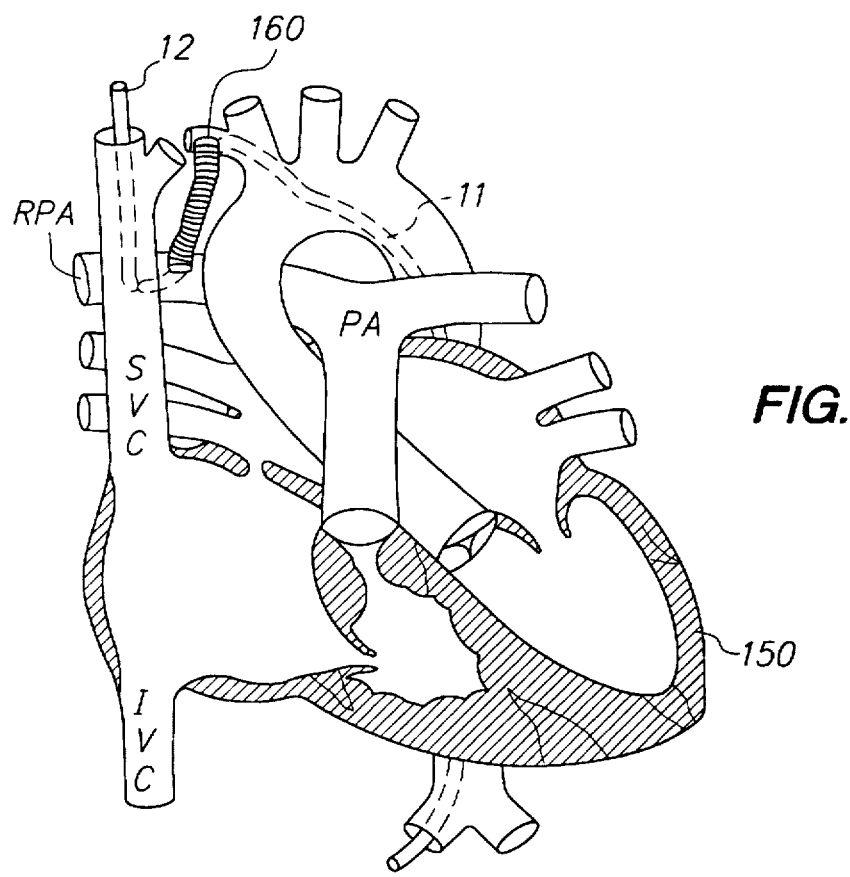
FIGS. 8A and 8B illustrate method steps of employing the apparatus of FIG. 1 to percutaneously perform a Glenn procedure.
Figure 8B:
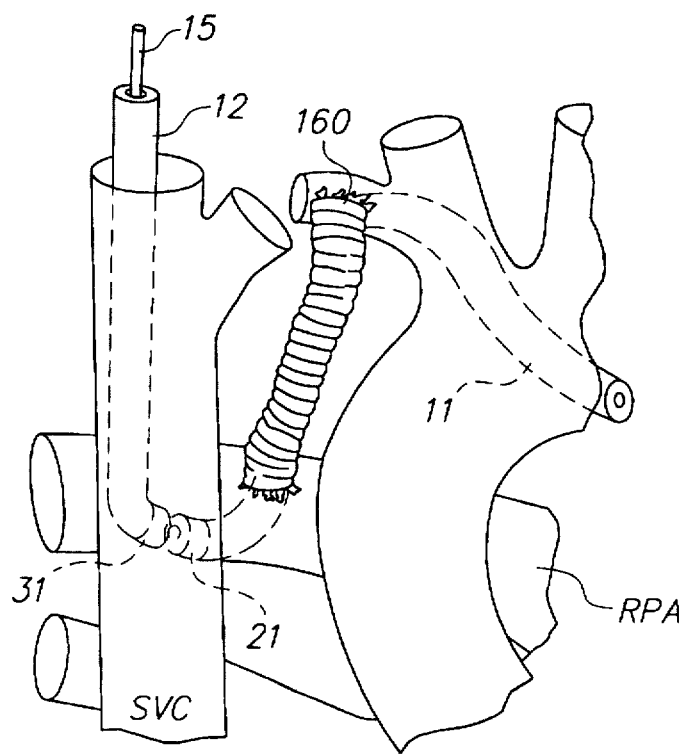

Referring now to FIGS. 8A and 8B, a method of percutaneously performing a bidirectional Glenn procedure is described, for example, to treat an atretic pulmonary valve. In FIG. 8A, heart 150 is shown wherein the pulmonary valve is obstructed due to a congenital lesion. B-T shunt 160 has previously been implanted between the subclavian artery and the right pulmonary artery in an earlier surgical stage.

In accordance with the present invention, catheter 11 is percutaneously routed via the subclavian artery (or the femoral artery and ascending aorta)and through the B-T shunt so that its distal end is positioned in right pulmonary artery RPA adjacent to superior vena cava SVC. Catheter 12 is inserted percutaneously via an access site in the jugular vein and through superior vena cava SVC so that its distal end is positioned opposite to the distal end of catheter 11. The positioning of the distal ends of catheters 11 and 12 may be confirmed, for example, using conventional fluoroscopic techniques. Power source 13 is then activated to energize electromagnets 21 and 31, thereby causing the distal ends of catheters 11 and 12 to attract one another and compress the vessel walls and tissue disposed therebetween.

Cutting wire 15 is advanced through catheter 12 so that it pierces the vessel wall of superior vena cava SVC, the intervening tissue, the wall of right pulmonary artery RPA, and passes into the lumen of catheter 11 with a trajectory predetermined by the spatial relation between the two catheters. Catheters 11 and 12 are then withdrawn while cutting wire 15 remains in place. A series of catheters of increasing diameter (or other suitable cutting device) are then deployed along the cutting wire (serving as a guide wire) to enlarge the opening through the extracorporeal passageway between the vessels. Once the opening has been sufficiently enlarged, the catheters or cutting device are removed. A prosthesis, such as graft or fluid impermeable stent, is then deployed (using the cutting wire as a guide wire) to maintain the patency of the passageway formed between the vessels.

Figure 9A:
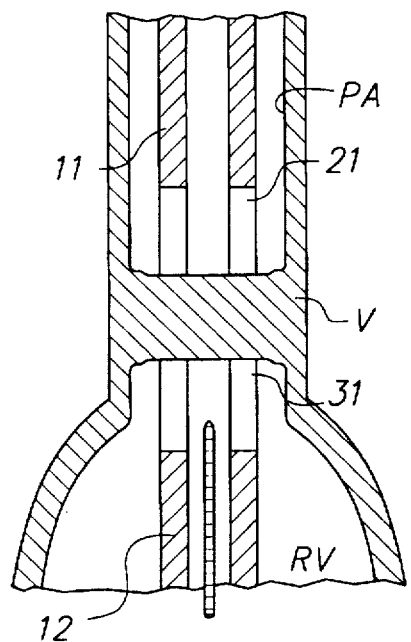
FIGS. 9A to 9C illustrate a method of employing the apparatus of the present invention to percutaneously open an atretic pulmonary valve.
Figure 9B:
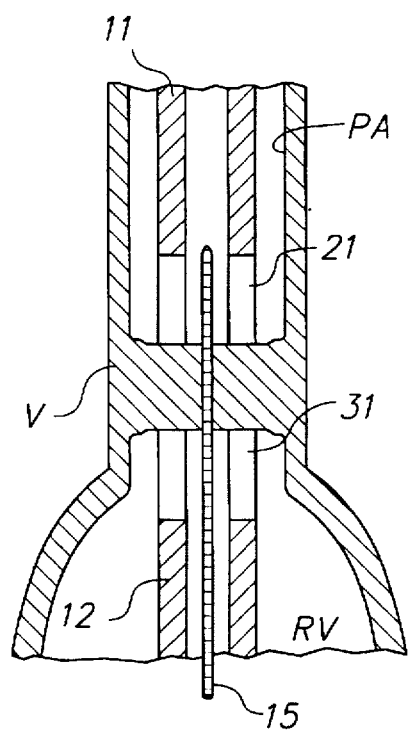
Figure 9C:
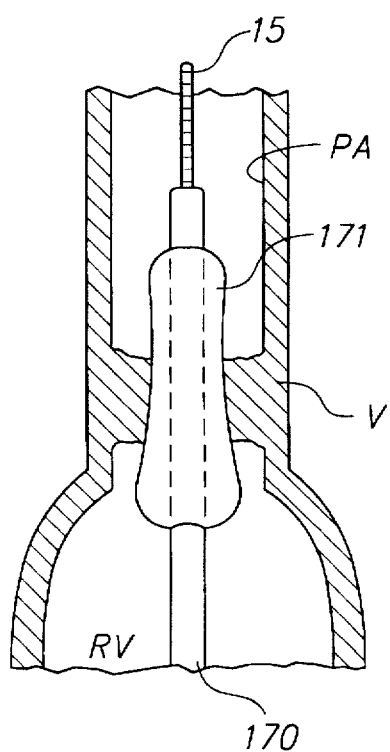

With respect to FIGS. 9A to 9C, an alternative method of percutaneously perforating an atretic pulmonary valve is described, involving formation of a passageway directly through the obstructed pulmonary valve. As shown in FIG. 9A, catheter 11 is inserted percutaneously via the femoral artery, aorta and patent ductus arteriosus into main pulmonary artery PA, so that the distal end of the catheter is positioned against obstructed pulmonary valve V. Catheter 12 is inserted via an access site at the femoral vein through the inferior vena cava, the right atrium and right ventricle RV, and is positioned against the opposing side of the obstructed pulmonary valve. Power source 13 is activated to energize electromagnets 21 and 31, causing the distal ends of catheters 11 and 12 to attract one another and compress the obstructed pulmonary valve therebetween.

In FIG. 9B, cutting wire 15 is advanced through catheter 12 so that it pierces obstructed valve V and passes into the lumen of catheter 11 with a trajectory predetermined by the spatial relation between the two catheters. Catheters 11 and 12 are then withdrawn while cutting wire 15 remains in place. As shown in FIG. 9C, catheter 170 having dilatation member 171 is inserted along cutting wire 15 (serving as a guide wire) and expanded to increase the diameter of the aperture formed through the valve. Alternatively, a series of catheters of increasing diameter, or other suitable cutting device (not shown) may be deployed along the cutting wire to enlarge the opening through the pulmonary valve. Once the opening through the valve has been sufficiently enlarged, the dilatation device or cutting device and cutting wire are removed.

As will be apparent to one of skill in the field of interventional cardiology, the method of forming a passageway through an obstruction in a vessel described hereinabove with respect to FIGS. 9A–9C may be readily employed in other clinical applications. For example, catheters constructed in accordance with the present invention may be advantageously employed to create a passageway through a vessel obstructed by plaque, such as in angioplasty, provided that the catheters may be disposed on either side of the obstruction.

Figure 10A:
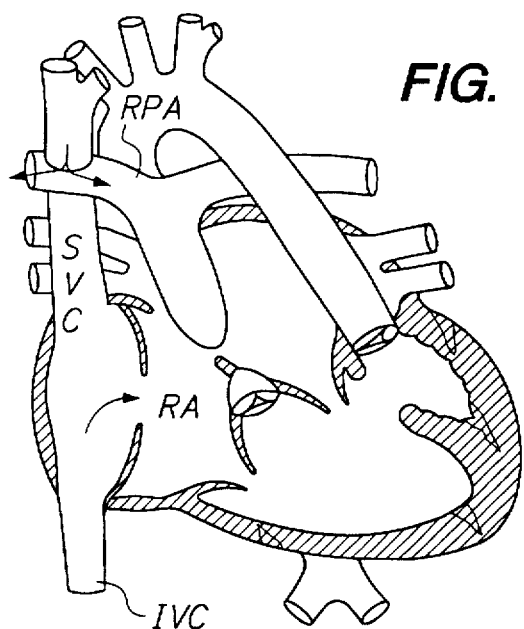
FIGS. 10A to 10C illustrate a method of employing the apparatus of the present invention to percutaneously perform the second stage of a Fontan procedure.
Figure 10B:
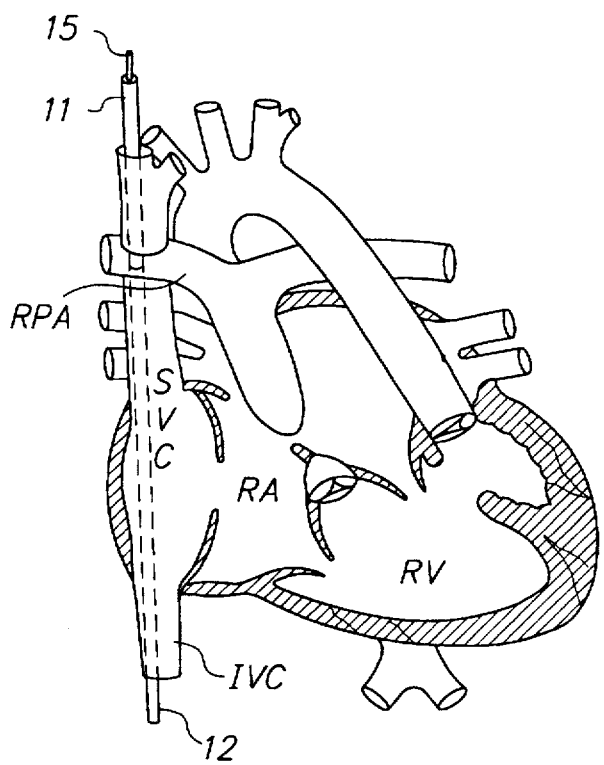
Figure 10C:
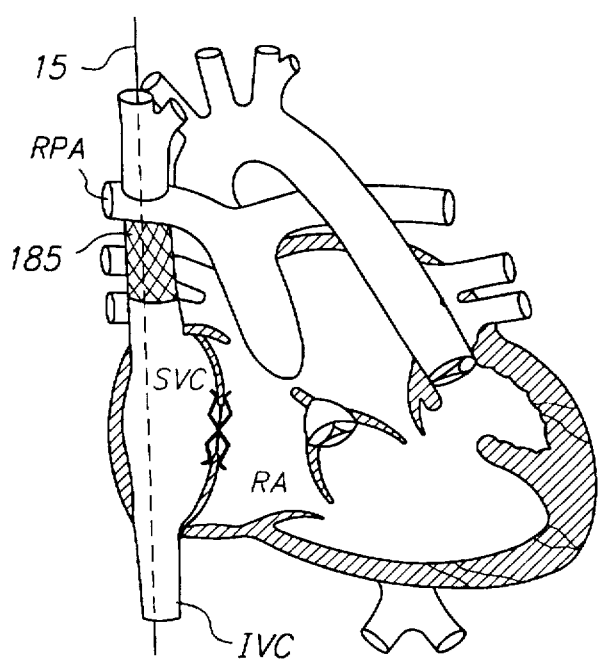

Referring now to FIGS. 10A to 10C, a method of employing the apparatus of the present invention to accomplish interventionally a-treatment stage of the Fontan procedure (that is conventionally accomplished by surgery) is described. The heart in FIG. 10A depicts a complex single ventricle anatomy, wherein the left ventricle is malformed and the ventricular septum and atrial septum are perforated. Treatment of this condition by the Fontan procedure typically involves two surgical stages. During the first step, a Glenn procedure is performed, in which the distal end of superior vena cava SVC is anastomosed to right pulmonary artery RPA, while the proximal end of superior vena cava SVC is occluded. A baffle is also placed across right atrium RA. In the second stage of the procedure, the proximal end of superior vena cava SVC is anastomosed to right pulmonary artery RPA and right atrium RA is completely closed off from inferior vena cava IVC and superior vena cava SVC.

In accordance with present invention, a Fontan procedure may be performed that involves only a single surgical stage followed by an interventional (percutaneous) stage. In the first stage, shown in FIG. 10A, the distal end of superior vena cava SVC is anastomosed to the superior wall of right pulmonary artery RPA, while the proximal end of the superior vena cava is sutured to the inferior wall of the right pulmonary artery in alignment with the anastomosis of the distal end of the superior vena cava. A baffle having, for example, a 30 mm diameter fenestration is implanted in the right atrium. The resulting blood flow pattern through the heart upon completion of the first stage is depicted by the arrows in FIG. 10A.

During a second interventional stage, catheter 11 is inserted via a jugular vein access site into superior vena cava SVC so that its distal end contacts the inferior wall of right pulmonary artery RPA. Catheter 12 is percutaneously inserted, for example, via the femoral vein, so that its distal end is positioned in the proximal end of the superior vena cava. Power source 13 is then activated to energize the electromagnets to attract one another across the thickness of the inferior wall of the right pulmonary artery.

Cutting wire 15 is then inserted through catheter 11 to form an opening between the inferior wall of right pulmonary artery RPA and the proximal end of superior vena cava SVC. Cutting wire 15 is retained in position and employed as a guide wire for the delivery of conventional stent 185 or a graft that seals the fenestration of the right atrium baffle at the same time. The embodiment of the apparatus of FIGS. 6A and 6B may be particularly advantageous for determining the correct positioning of the stent or graft prior to deployment. The fenestration in the baffle may also be closed employing a previously known hole closure device and delivery system, as described, for example, in U.S. Pat. No. 5,334,217 to Das, U.S. Pat. No. 5,108,420 to Marks or U.S. Pat. No. 3,874,388 to King et al. At the conclusion of the second stage, the Fontan procedure is complete, with all blood flow to the right heart rerouted to the pulmonary artery via the bidirectional Glenn anastomoses.

The foregoing applications of the apparatus and methods of the present invention are merely illustrative. It will be apparent to those of skill in the art that the apparatus of the present invention may be readily used in other applications to percutaneously perform entire procedures, or at least stages of procedures, which heretofore could be accomplished only surgically. Accordingly, various changes and modifications may be made therein without departing from the invention, and the appended claims are intended to cover all such changes and modifications that fall within the true spirit and scope of the invention.

What is claimed is:

1. Apparatus for forming a passageway through tissue comprising:

a first catheter shaft having proximal and distal ends and a portion defining a first lumen extending from the proximal end to the distal end;

a first electromagnet disposed on the distal end of the first catheter;

means for cutting tissue disposed in the first lumen;

a second catheter shaft having proximal and distal ends and a portion defining a second lumen that extends proximally from the distal end;

a second electromagnet disposed on the distal end of the second catheter; and means for selectively energizing the first and second electromagnets, wherein the first and second electromagnets attract one another when disposed in opposition across a thickness of tissue and the first lumen is aligned with the second lumen, the means for cutting extending from the first lumen into the second lumen to cut a passageway through the thickness of tissue.

2. The apparatus as defined in claim 1 wherein the means for cutting comprises a flexible wire having a sharpened tip.

3. The apparatus as defined in claim 1 wherein the first catheter shaft has a longitudinal axis, the first catheter shaft further comprising means for deflecting the distal end of the first catheter away from the longitudinal axis.

4. The apparatus as defined in claim 1 wherein the electromagnet comprises an annular element comprising a ferromagnetic material, and a coil of electrically insulated wire wrapped around the annular element.

5. The apparatus as defined in claim 1 wherein the electromagnet comprises a plurality of circumferential segments.

6. The apparatus as defined in claim 1 wherein the first lumen exits through a lateral wall of the first catheter.

7. The apparatus as defined in claim 1 wherein the second lumen extends from the distal end to the proximal end of the second catheter.

8. The apparatus as defined in claim 1 wherein the means for cutting comprises a flexible wire having a sharpened tip and a plurality of barbs projecting from the flexible wire proximal of the sharpened tip, and the second lumen includes means for engaging the plurality of barbs.

9. The apparatus as defined in claim 1 wherein the portion of the second catheter defining the second lumen includes a portion defining a conical region that assists in guiding the means for cutting into the second lumen.

10. A kit for forming a passageway through tissue comprising:

a first catheter shaft having proximal and distal ends and a portion defining a first lumen extending from the proximal end to the distal end;

a first electromagnet disposed on the distal end of the first catheter;

a second catheter shaft having proximal and distal ends and a portion defining a second lumen that extends proximally from the distal end;

a second electromagnet disposed on the distal end of the second catheter;

means for selectively energizing the first and second electromagnets; and a flexible wire disposed in the first lumen, the flexible wire having a sharpened tip, wherein the first and second electromagnets attract one another when disposed in opposition across a thickness of tissue and the first lumen is aligned with the second lumen, so that when the flexible wire is extended from the first lumen it cuts a passageway through the thickness of tissue and enters the second lumen.

11. The kit as defined in claim 10 wherein the first catheter shaft has a longitudinal axis, the first catheter shaft further comprising means for deflecting the distal end of the first catheter away from the longitudinal axis.

12. The kit as defined in claim 10 wherein the first electromagnet comprises a plurality of circumferential segments formed of a ferromagnetic material, and a coil of electrically insulated wire wrapped around each one of the plurality of circumferential segments.

13. The kit as defined in claim 10 wherein the first lumen exits through a lateral wall of the first catheter.

14. The kit as defined in claim 10 wherein the second lumen extends from the distal end to the proximal end of the second catheter.

15. The kit as defined in claim 10 wherein the flexible wire further comprises a plurality of outwardly projecting barbs positioned proximal of the sharpened tip, and the second lumen includes means for engaging the plurality of barbs.

16. A method of forming a passageway through tissue comprising steps of:

providing a first catheter having a first lumen, a first distal end, and a first electromagnet disposed on the first distal end, a second catheter having a second lumen, a second distal end, and a second electromagnet disposed on the second distal end, a flexible wire having a sharpened tip, and means for selectively energizing the first and second electromagnets;

inserting the first catheter into a first body vessel or organ so that the first distal end is located against a first wall;

inserting the second catheter into a second body vessel or organ so that the second distal end is located against a second wall in opposition to the first distal end;

energizing the first and second electromagnets to cause the first distal end to attract the second distal end and align the first lumen with the second lumen;

advancing the flexible wire through the first lumen so that the sharpened tip exits the first lumen, punctures the first and second walls, and enters the second lumen.

17. The method as defined in claim 16 further comprising steps of extending the flexible wire through the second lumen, and removing the first and second catheters while leaving the flexible wire in place.

18. The method as defined in claim 17 further comprising a step of using the flexible wire as a guide wire while enlarging the passageway.

19. The method as defined in claim 16 to percutaneously perform a bidirectional Glenn procedure on a heart having a B-T shunt, wherein the step of inserting the first catheter comprises a step of inserting the first catheter through a vein and into the superior vena cava, so that the first distal end is located against the wall of the superior vena cava adjacent the right pulmonary artery, and the step of inserting the second catheter comprises a step of inserting the second catheter through a femoral artery, the aorta, the subclavian vein and the B-T shunt and into the right pulmonary artery, so that the second distal end is located against the wall of the right pulmonary artery in opposition to the first distal end.

20. The method as defined in claim 16 to percutaneously perform the second stage of a Fontan procedure, wherein during a first surgical stage the distal portion of the superior vena cava is anastomosed to the superior wall of the right pulmonary artery, the proximal portion of the superior vena cava is sutured to the inferior wall of the right pulmonary artery, and a fenestrated baffle is implanted in the right atrium, the second stage comprising steps wherein the step of inserting the first catheter comprises inserting the first catheter via a vein, through the superior vena cava and the anastomosis to the right pulmonary artery, so that the first distal end is located against the internal inferior wall of the right pulmonary artery, wherein the step of inserting the second catheter comprises the step of inserting the second catheter via a femoral vein and the inferior vena cava so that the second distal end is located against the exterior of the inferior wall of the right pulmonary artery, the step of advancing the flexible wire forming a passageway from the proximal end of the inferior vena cava to the right pulmonary artery, the method further comprising steps of:

deploying a stent or graft in the passageway; and deploying a hole closure device in the fenestration of the baffle to isolate the vena cava from the right atrium.

* * * * *